United States Patent [19]

Sørensen

[11] Patent Number: 4,518,566

[45] Date of Patent: May 21, 1985

[54] DEVICE FOR DETERMINING THE CONCENTRATION OF AN ABSORBABLE COMPONENT IN A GASEOUS MIXTURE

[76] Inventor: Ansgar C. H. Sørensen, Anemonevej 4, Allerod, Denmark, DK-3450

[21] Appl. No.: 495,991

[22] Filed: May 19, 1983

Related U.S. Application Data

[62] Division of Ser. No. 287,728, filed as PCT DK 80/00072, Nov. 19, 1980, published as WO 81/01615 Jun. 11, 1980, § 102(e) date Jul. 24, 1981, Pat. No. 4,407,963.

[30] Foreign Application Priority Data

Nov. 30, 1979 [DK] Denmark ............................ 5100/79

[51] Int. Cl.³ ............................................ G01N 31/06
[52] U.S. Cl. ........................................ 422/88; 73/25; 374/12; 374/54; 436/147
[58] Field of Search ................... 261/79 A, 117; 73/19, 73/25; 374/31, 10, 12, 45, 54; 422/51, 86, 88, 90; 436/147

[56] References Cited

U.S. PATENT DOCUMENTS

| | | | |
|---|---|---|---|
| 847,552 | 3/1907 | Carlson | 261/79 A |
| 3,702,048 | 11/1972 | Horwick | 261/79 A X |
| 3,716,337 | 2/1973 | Jones | 436/147 X |
| 4,042,328 | 8/1977 | Seymour | 436/100 X |
| 4,251,497 | 2/1981 | Tezuka et al. | 436/147 X |
| 4,299,593 | 11/1981 | Dopp | 436/164 X |
| 4,320,092 | 3/1982 | Kondo et al. | 261/79 A X |

FOREIGN PATENT DOCUMENTS

| | | | |
|---|---|---|---|
| 105379 | 10/1938 | Austria | 436/147 |
| 823807 | 10/1951 | Fed. Rep. of Germany . | |
| 2165759 | 7/1973 | Fed. Rep. of Germany . | |
| 2225889 | 12/1973 | Fed. Rep. of Germany . | |
| 2406200 | 5/1979 | France . | |
| 1431095 | 4/1976 | United Kingdom . | |

Primary Examiner—Barry S. Richman
Assistant Examiner—Robert J. Hill, Jr.
Attorney, Agent, or Firm—Watson, Cole, Grindle & Watson

[57] ABSTRACT

A measuring device for determining the concentration of an absorbable component in a gaseous mixture includes a vertically oriented tubular housing, a vertical hollow tube positioned within the housing and having a heat conducting wall and an open mouth at its upper end; a stub connected to the lower end of the vertical tube for passing a stream of liquid absorbent upwardly through the vertical tube so as to form a free surface area above the mouth of the tube, the liquid absorbent overflowing along the outside of the hollow tube; a stub connected to the housing at a point above the upper end of the vertical tube therein for passing a flow of gaseous mixture past the free surface of the absorbent; a first temperature sensor within the vertical tube adjacent the mouth thereof and covered by the liquid absorbent flowing out of the mouth of the tube; and a second temperature sensor located within the housing to measure the temperature of the gaseous mixture immediately before it contacts the liquid absorbent at the upper end of the tube.

3 Claims, 4 Drawing Figures

DEVICE FOR DETERMINING THE CONCENTRATION OF AN ABSORBABLE COMPONENT IN A GASEOUS MIXTURE

CROSS-REFERENCE TO RELATED APPLICATION

This application is a divisional application of application Ser. No. 287,728, filed as PCT DK 80/00072, Nov. 19, 1980, published as WO 81/01615 Jun. 11, 1980, § 102(e) date July 24, 1981, now U.S. Pat No. 4,407,963.

BACKGROUND OF THE INVENTION

1. Field of the Invention

The present invention relates to a method for determining the concentration of an absorbable component in a gaseous mixture.

2. The Prior Art

A great many widely differing methods for determining the content of individual components in gaseous mixtures are known. These methods are based on physical, physico-chemical or purely chemical properties of the component which is to be determined in relation to the other components in the gaseous mixture.

One group of methods is based on the isolation of the component in question from the gaseous mixture by absorbing it in a suitable absorption liquid, whereby according to circumstances the absorption may be purely physico-chemical in nature or may be accompanied by a chemical reaction. The subsequent measurement of the quantity absorbed may then be performed by chemical methods or by measuring appropriate concentration-related physical or physico-chemical properties of the liquid phase.

In accordance with an existing absorption method, a stream of absorbent material of known size is brought into intimate contact with a stream of known size of a gaseous mixture of which the concentration of a given component is to be determined. The choice of a suitable absorbent material will ensure that the absorption process will be accompanied by a change in the heat content, which will cause the heating up of the mixture of the stream of absorbent material and the stream of gas. Under certain circumstances, this rise in temperature will provide an indication of the concentration of the absorbed component in the gas flow. The method calls for the effective thermal insulation of the absorption section, just as it demands the precise metering of the size of both the stream of absorbent material and the stream of liquid, these streams being brought into thermal equilibrium before absorption takes place. The resulting increase in temperature will more often than not be very small and will require precise measuring equipment. The time constant for the measurements is highly significant in view of the thermal capacity and conductivity of the walls and of the insulating material.

SUMMARY OF THE PRESENT INVENTION

The method for determining the concentration of an absorbable component in a gaseous mixture in accordance with the present invention is characterized in that a gaseous stream containing the component of which the concentration in the gas flow is to be determined, hereinafter referred to as A, is brought into contact with a stream of absorbent material in liquid form which is capable of absorbing the component in question in such a way that:

(a) the resistance to the absorption process will mainly exist in the gaseous phase;
(b) the equilibrium concentration of A above the absorbent material will be negligible in proportion to the concentration of A in the gaseous stream;
(c) the absorption process will be associated with a heat content change;
(d) the stream of absorbent material will, before it is brought into contact with the gaseous stream, be heated to a temperature close to the temperature which the stream of absorbent material will try to reach when it is brought into contact with the gas flow;
(e) the temperature of the absorbent material at the point at which it is first exposed to the gas flow, hereinafter referred to as the point of measurement, will be measured with the help of a suitable temperature sensor, and that the temperature of the gas flow will be measured at a point adjacent to the aforementioned point of measurement, although at a sufficient distance from it for the temperature and the composition of the gas flow not to be influenced by the absorption process;
(f) the contact surface between the gas flow and the absorbent material at the point of measurement will be provided with a permanent supply of fresh absorbent material;
(g) the flow of absorbent material will be chosen in such a way that the area surrounding the point of measurement will be completely moistened by the absorbent material at all times.

An embodiment of an apparatus for performing the method in accordance with the present invention is characterized in that it consists of a vertical tube through which the stream of absorbent material is passed in an upward direction before it is brought into contact with the gas flow, wherein the gas flows around the tube in an essentially downward direction or in an essentially horizontal direction. The tube is open at its top, and a temperature sensor is fitted directly inside or adjacent to the mouth. The stream of absorbent material flows out through the upper mouth of the tube, the absorbent material completely surrounding the temperature sensor and flowing in the form of a thin film downwardly along the outside of the tube in contact with the surrounding gas flow.

The method for determining the concentration of an absorbable component in a gaseous stream depends, in the case of the present invention, upon the fact that a condition of dynamic equilibrium is created when contact takes place between the gas flow and a stream of absorbent material, since the stream of absorbent material will absorb the component A from the gas flow when contact takes place between the two at the free surface area of absorbent material formed at the upper end of the tube. During the absorption process, which may be purely physical in nature or may be accompanied by one or more chemical reactions in the absorbent material, heat is released, hereinafter referred to as absorption heat, causing the temperature of the absorbent material to increase at its free surface area. In this way the absorbent material will reach a higher temperature than the adjoining gas flow, with the result that heat will be transferred by convection from the free surface of the absorbent material to the gas flow, although a proportion of the heat released during the absorption process will, unless special measures are taken to prevent this, be carried away with the stream of absorbent material in the form of sensible heat.

The temperature of the free surface of absorbent material will increase until the point is reached at which the quantity of heat which is released per unit of time during the absorption process is identical to the quantity of heat which is removed per unit of time. The temperature which the absorbent material adopts in this way will be referred to below as the "dynamic equilibrium temperature". By heating the absorbent material to that temperature before it is brought into contact with the gas flow, the dynamic equilibrium temperature will not be dependent upon the size of the stream of absorbent material, since the entire quantity of heat released during the absorption process will then be transferred to the adjoining gas flow, ignoring the possibility of a small loss by radiation from the surface of the absorbent material to the surrounding walls. Since the concentration of the absorbed component A at free surface of the absorbent material is insignificantly small in relation to the concentration of A in the undisturbed gas flow, it may be stated with a high degree of approximation that the rate at which A is absorbed, and thus the rate at which heat is generated, will be proportional to the concentration of A in the gas flow.

The difference in temperature which occurs between the free surface of the absorbent material and the gas flow, the temperature difference being the reason why the absorption heat which is released may be transferred to the gas flow, is also proportional to the quantity of heat released per unit of time with the result that proportionality exists between the concentration of A in the gas flow and the overtemperature of the absorbent material in relation to the surrounding undisturbed gas flow. Thus the concentration of A in the gas flow may be determined by measuring that temperature difference. Both the transfer of A from the gas flow to the free surface of the absorbent material and the transfer in the opposite direction of heat from the surface of the absorbent material to the gas flow take place by convection. Any changes in the speed or direction of the gas flow past the surface of the absorbent material will therefore affect both the absorption process and the transfer of heat to the same degree and will not accordingly change the relationship between the temperature difference between the surface of the absorbent material and gas flow and the concentration of the component A in the gas flow. The existence of a constant relationship between the two aforementioned values is also conditional upon the relationship between the area of the contact surface through which the transfer of heat to the gas flow takes place and the area of the contact surface through which the absorption takes place also being constant. This will be the case if the area surrounding the point of measurement is completely covered by the stream of absorbent material at all times, when the two contact surfaces will be identical.

The rate of absorption will rise with increasing concentration of A in the gas flow, just as the speed and direction of the gas flow in relation to the surface of the absorbent material will have an effect on the rate at which absorption takes place.

The result of absorption is an accumulation of A at the surface of the absorbent material, and if no provision is made for the adequate replacement of the surface of the absorbent material at the point of measurement by the supply of fresh, undiluted absorbent material, the concentration of A in the gaseous phase directly at the surface will increase and will gradually reach a size which may not be ignored by comparison with the concentration of A in the undisturbed gas flow. When this occurs, the rate of absorption will be highly dependent upon the conditions of concentration and the temperature at the surface of the absorbent material, thus invalidating the basic principle of the method of measurement. The requirement for the surface to be replaced grows with the increase in the concentration of A in the gas flow and sets an upper limit to the size of the concentrations which may be determined directly by the use of this method of measurement. In addition to depending on the concentration of A in the gas flow, this limit will also depend on the geometrical shape of the measuring instrument used for carrying out the method and on the temperature, speed and direction of the gas flow.

The quantity of heat released by the absorption of a given quantity of the component A will normally depend on both the conditions of concentration within the absorbent material and its temperature. The dependence of the absorption heat on the concentration will normally require the surface of the absorbent material at the point of measurement to have a constant level of concentration, whereas the effect of the temperature on the absorption heat will be so low in the majority of cases that only rarely will it be necessary to take it into consideration, which may be done, furthermore, since the absorption temperature has a known value, as it is identical to the dynamic equilibrium temperature.

The gas speed past the measuring instrument is of significance to the rate at which the dynamic equilibrium temperature of the stream of absorbent material will be reached, since any increase in the gas speed will cause the point of equilibrium to be reached more quickly due to the higher heat and material transfer coefficients involved in the exchange of heat and material between the gas flow and the stream of absorbent material. Since any increase in the gas speed will involve an increase in the rate of heat transmission by convection, but without any variation in the dynamic equilibrium temperature, the relative significance of the possible loss by radiation from the surface of the absorbent material to the surroundings will fall as the gas speed increases. For these reasons, then, a high gas speed past the measuring instrument is desirable to the extent that it may be combined with the requirement for the adequate effective replacement of the surface of the absorbent material at the point of measurement.

The method described here makes possible the precise and continuous determination of the concentration of an absorbable component in a gaseous mixture. The time constant for the measurement may be varied within wide limits by the appropriate geometrical design of and by the selection of an appropriate gas speed past the point of measurement.

Over a wide range, the reading will be unaffected by the temperature and pressure of the air stream and by its speed past the point of measurement, just as the reading will be insensitive to variations in the size and temperature of the stream of absorbent material.

The method described here also permits the determination of the concentration to be unaffected by the presence of inert dust in the gas flow, since the contact surface between the absorbent material and the gas flow is continually being replaced at the point of measurement. Nevertheless, the measurement will be distored by the presence of any dust which is capable of reacting with the absorbent material accompanied by heat content change.

The method described here is an absolute method for the determination of concentration and as such requires no prior calibration. The difference in temperature measured by this method between the absorbent material and the gas flow provides a measure of the mole fraction or of the volume concentration of the absorbable component, since the recorded increase in temperature is very near proportional to that concentration.

In a simple embodiment of the measuring apparatus for carrying out the method the gas flow in which the concentration of A is to be determined is brought into contact with the surface of the absorbent material without undergoing any prior treatment.

However, so as to be able to determine the concentration of A in gas streams in which the content of A is so high that if the gas stream were directly applied to the free surface of the absorbent material, condition (b) above would no longer be fulfilled, it may be expedient before determining the concentration by means of the method in accordance with the present invention to dilute the gas flow with a stream of A-free gas in a known proportion. This stream of gas may either be introduced from a source outside the measuring apparatus or may be produced by purifying the gas flow which has already passed the point of measurment of its content of the component A with the help of a suitable absorption or adsorption medium. The gas flow which has thus been purified is then divided into two streams in a pre-determined proportion, whereupon one of the streams is mixed with the gas flow of which the content of A is to be determined. The other stream is discarded and, provided that the apparatus is sealed from the surroundings, will contain the same quantity of gas as the quantity of inert gas contained in the supply of undiluted gas containing the component A.

It may also be found to be expedient in accordance with the present invention to equip the measuring apparatus with a means of regenerating the absorption or adsorption medium. Where concentrated sulphuric acid is used as the absorbent material when determining the water content of air, the measuring apparatus may then be equipped with a distillation column for the purpose of re-concentrating the used sulphuric acid.

When measuring gas flows at high temperatures, it may be found to be expedient in accordance with the present invention to cool the flow before it is applied to the free surface area of the absorbent material.

When measuring the concentration of A in gas flows with a very low A-content, it may also be found to be expedient in accordance with the present invention to bring the gas flow and the stream of absorbent material into concurrent thermal contact with each other, so that they are fed into the central section of the measuring apparatus at approximately the same temperature.

By selecting an appropriate absorbent material, the method described here may be used for determining the concentration of a large number of components, including technically important substances such as $H_2O$, $CO$, $CO_2$, $SO_2$, $O_2$ and $NO_2$. The following is a list of examples of different types of absorbent material:

(a) Acids, such as sulphuric acid and phosphoric acid;
(b) Bases, such as sodium hydroxide, sodium carbonate, amines and ammonia solutions;
(c) Oxidizing agents, such as potassium permanganate, potassium dichromate and sodium peroxide;
(d) Reducing agents, such as sodium hyposulphite and pyrogallol;
(e) Complexing agents, such as ammoniacal solutions of copper salts.

The absorbent material may be in the form of either a true liquid or a fluid suspension and may contain dissolved or solid catalysts.

For example, the water vapour concentration in an air mixture may be determined by the use of concentrated sulphuric acid as the absorbent material, since the partial equilbrium pressure of water vapour over 98% sulphuric acid is less than 0.1 mm of mercury at 200° C. A series of tests were conducted in a measuring cell of the type illustrated in FIG. 1. The stream of absorbent material was regulated between 10 ml/h and 30 ml/h, and the air flow was regulated between 250 l/h and 1000 l/h. The temperature of the air supply varied between 20° C. and 60° C. At water vapour concentrations of up to 3.5 mol %, no dependency on the test parameters which were applied was observed, since a linear relationship was found to exist irrespective of the test conditions between the water vapour concentration in the air and the temperature difference of the stream of sulphuric acid in relation to the surrounding air flow. The recorded temperature rise amounted to about 25° C. per mol% of water vapour in the air.

The invention will now be better understood by reference to the attached drawings.

DETAILED DESCRIPTION OF THE DRAWINGS

Figure 1A:
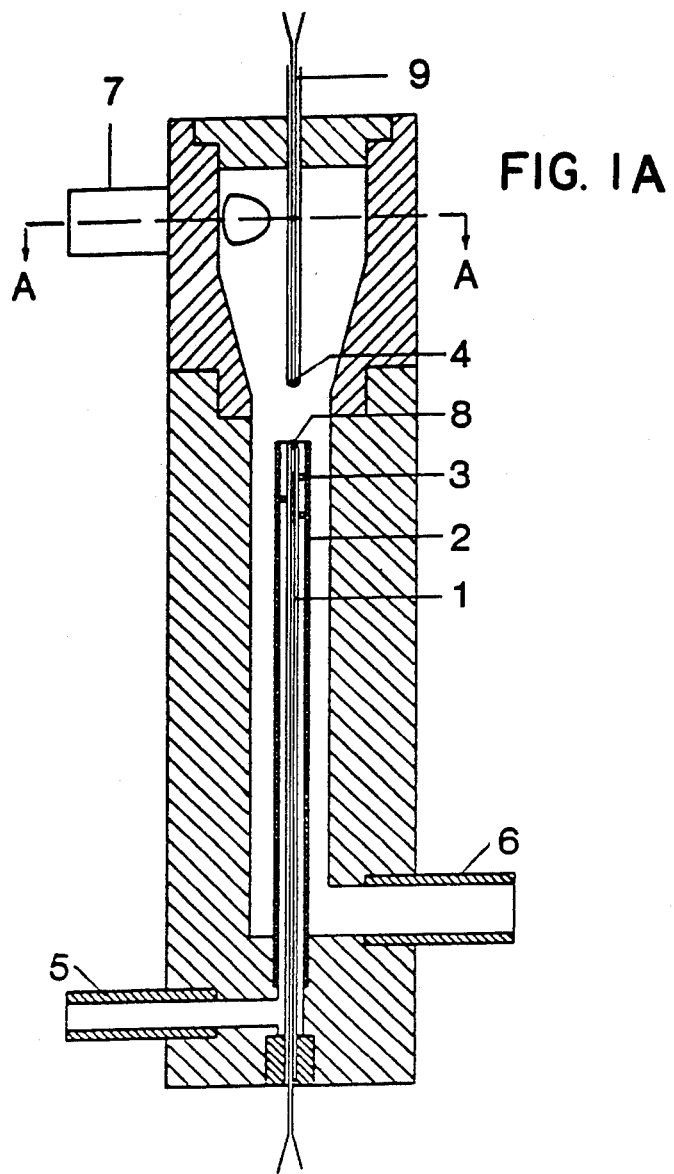
FIG. 1A shows a cross sectional side view of one type of measuring cell which can be used to accomplish the method of the present invention.
Figure 1B:
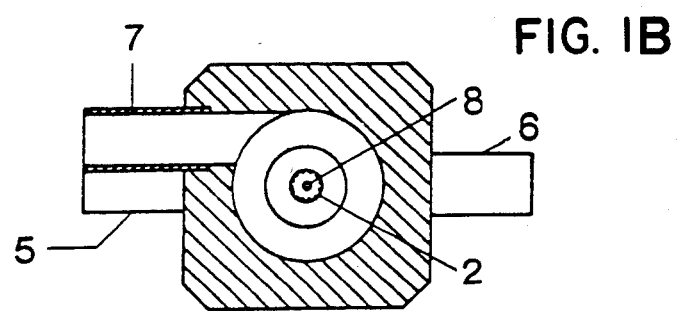
FIG. 1B shows a view of the measuring cell of FIG. 1A as seen along line A—A.

The measuring cell shown in FIGS. 1A and 1B is a throughflow cell which consists of a housing with a central bore through which the gas stream which is to be tested is passed in a downward direction, the gas entering through a pipe stub 7 and leaving through a second stub 6.

The stream of absorbent enters through a stub 5 and moves upwardly through a tube 2 having a heat conducting wall. From the top of this tube the spent absorbent moves downwardly under the effect of gravity in the form of a stream along the outside of the tube in contact with the gas stream and in heat exchange relationship with the upward stream of fresh absorbent in the interior of the tube through the heat-conducting wall of the tube, whereby the stream of fresh absorbent will be heated or cooled by the stream of spent absorbent to a temperature close to the dynamic equilibrium temperature. In the embodiment shown, the stream of absorbent leaves through the stub 6 together with the gas stream.

At the upper end of the tube, where the fresh absorbent forms a free surface area which is exposed to the gas stream of which the concentration of the absorbable component is to be determined, is located a thermoelement 8, housed in a protective casing 1, which passes up through the tube 2 and is held concentrically inside the tube by means of a spiral 3.

Above the tube 2 and at a small distance from it is located a second thermoelement 4 of the same type as the thermoelement 8 and, like the thermoelement 8, is housed in a protective casing 9.

Figure 2A:
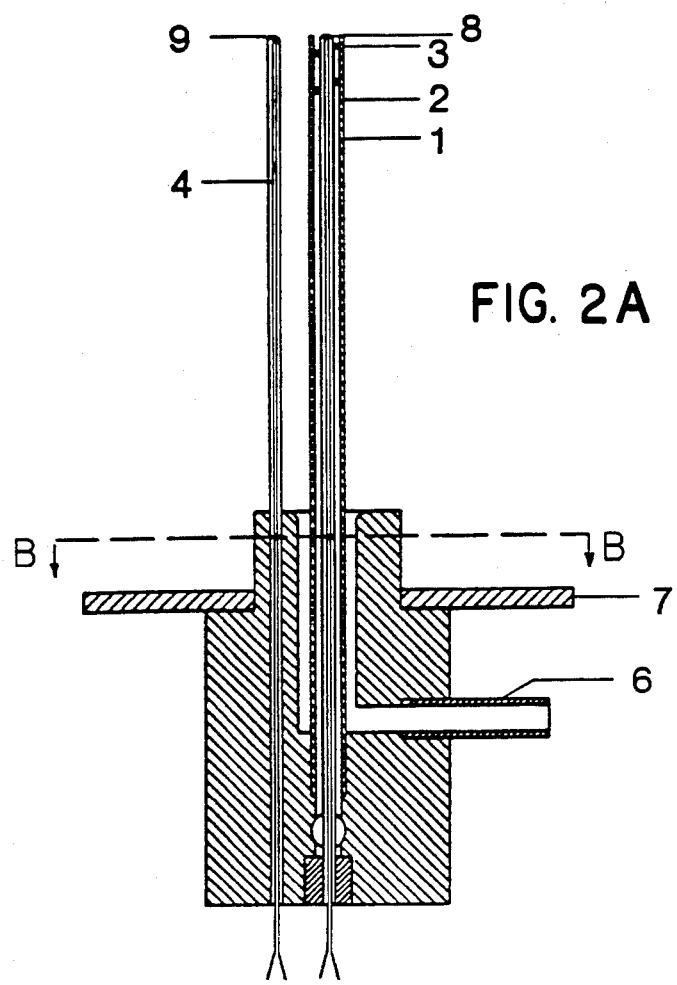
FIG. 2A shows a cross sectional side view of another type of measuring cell which can be used to accomplish the method of the present invention.
Figure 2B:
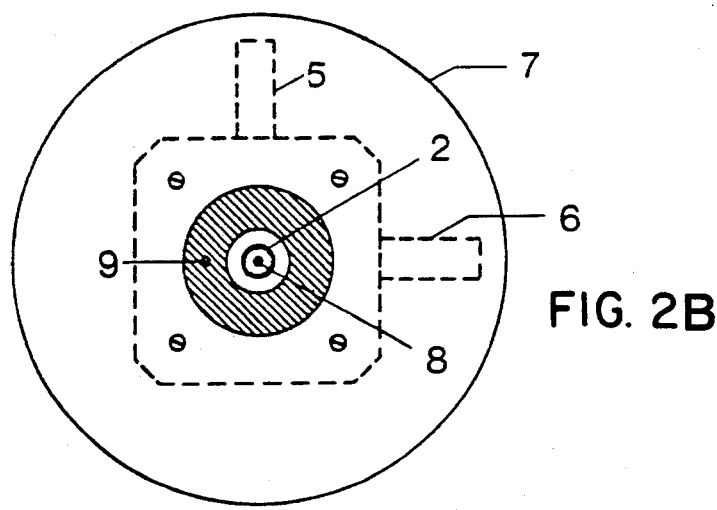
FIG. 2B shows a view of the measuring cell of FIG. 2A as seen along line B—B.

FIGS. 2A and 2B show a measuring apparatus for direct installation in a horizontal channel or similar. The apparatus consists of a solid block with bores, in which is installed a vertical open tube 2. The absorbent enters through a stub 5 and flows to the top of the tube 2, from where the absorbent materials runs down the outside of the tube and leaves through the stub 6.

At the upper mouth of the tube 2 is located a thermoelement 8 surrounded by a protective casing 1, which is held concentrically inside the tube 2 by means of a spiral 3.

A second thermoelement 9 of the same type as the thermoelement 8 is housed inside a protective casing 4. When installing the measuring apparatus, the thermoelement 9 is positioned in such a way that the gas flow will meet the thermoelement before the gas flow meets the tube 2.

A location flange 7 is used to secure the apparatus to the wall of the channel.

I claim:

1. A measuring device for determining the concentration of an absorbable component in a gaseous mixture comprising a vertical hollow tube having a heat conducting wall and an open mouth at its upper end, means for passing a stream of liquid absorbent upwards through said tube at a rate such that the liquid absorbent is not sprayed out of the mouth of the tube but remains in contact with the tube so as to form above said mouth a free surface area from which the liquid absorbent overflows along the outside of the tube, means adjacent the upper end of said tube for passing a flow of a gaseous mixture past the upper end of said tube and said free surface area of absorbent and in surface contact therewith, a first temperature sensor being disposed in said tube and being fitted adjacent the mouth of the tube in a location such as to be completely covered by the liquid absorbent flowing out of the mouth of said tube, a supporting member extending up through the tube and supporting, at its top, said first temperature sensor, and a second temperature sensor being positioned adjacent to said first temperature sensor and upstream thereof so that said gaseous mixture contacts said second temperature sensor prior to contacting the upper end of said tube so as to measure the temperature of said gaseous mixture immediately before it arrives into contact with the absorbent at the upper end of the tube.

2. A device as defined in claim 1, wherein said supporting member is a protective casing for said first temperature sensor.

3. A device as defined in claim 1, wherein said supporting member is held concentrically inside said tube by means of a spiral member.

* * * * *